United States Patent
Iizuka

(10) Patent No.: US 9,949,619 B2
(45) Date of Patent: Apr. 24, 2018

(54) ENDOSCOPE

(71) Applicant: OLYMPUS CORPORATION, Tokyo (JP)

(72) Inventor: Tomoyuki Iizuka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/265,025

(22) Filed: Sep. 14, 2016

(65) Prior Publication Data

US 2017/0000319 A1    Jan. 5, 2017

Related U.S. Application Data

(63) Continuation of application No. PCT/JP2015/060465, filed on Apr. 2, 2015.

(30) Foreign Application Priority Data

Aug. 6, 2014    (JP) .............................. 2014-0160714

(51) Int. Cl.
*A61B 1/00* (2006.01)
*A61B 1/018* (2006.01)
(Continued)

(52) U.S. Cl.
CPC ............ *A61B 1/00142* (2013.01); *A61B 1/00* (2013.01); *A61B 1/0014* (2013.01);
(Continued)

(58) Field of Classification Search
CPC ............ A61B 1/00101; A61B 1/00103; A61B 1/0008
(Continued)

(56) References Cited

U.S. PATENT DOCUMENTS 4,794,911 A * 1/1989 Okada ................ A61B 1/00096
600/127
4,881,810 A * 11/1989 Hasegawa .......... A61B 1/00101
356/241.5
(Continued)

FOREIGN PATENT DOCUMENTS

JP    S57-87704    5/1982
JP    H09-75296 A    3/1997
(Continued)

OTHER PUBLICATIONS

International Search Report dated Jun. 23, 2015 issued in PCT/JP2015/060465.
(Continued)

*Primary Examiner* — Matthew J Kasztejna
(74) *Attorney, Agent, or Firm* — Scully, Scott, Murphy & Presser, P.C.

(57) ABSTRACT

An endoscope according to the invention includes a distal end member of an endoscope main body, a guide groove provided in the distal end member from a proximal end side toward a distal end side, first and second concave sections provided at a proximal end and a distal end in the guide groove, a cover attached to the distal end member, and a convex section provided in the cover, the convex section sliding in the guide groove to selectively engage with the first concave section and the second concave section. The convex section engages with the first concave section to fix the cover to the distal end member. The convex section is slid along the guide groove and engages with the second concave section to fix the cover to the distal end member in a state in which the cover deviates to the distal end side.

7 Claims, 8 Drawing Sheets

(51) Int. Cl.
*G02B 23/24* (2006.01)
*A61B 18/00* (2006.01)

(52) U.S. Cl.
CPC .......... *A61B 1/00177* (2013.01); *A61B 1/018* (2013.01); *G02B 23/243* (2013.01); *A61B 1/0008* (2013.01); *A61B 1/00101* (2013.01); *A61B 2018/00101* (2013.01); *A61B 2018/00982* (2013.01)

(58) Field of Classification Search
USPC ................................................ 600/127, 129
See application file for complete search history.

(56) References Cited

U.S. PATENT DOCUMENTS

| | | | | |
|---|---|---|---|---|
| 5,104,379 A * | 4/1992 | Nakamura | ......... | A61B 1/00062 604/111 |
| 5,662,588 A * | 9/1997 | Iida | .................... | A61B 1/00091 600/121 |
| 5,674,181 A * | 10/1997 | Iida | ...................... | A61B 1/0008 600/121 |
| 5,730,701 A | 3/1998 | Furukawa et al. | | |
| 5,746,695 A * | 5/1998 | Yasui | ................. | A61B 1/00091 600/121 |
| 5,788,628 A * | 8/1998 | Matsuno | ............ | A61B 1/00091 600/121 |
| 5,860,913 A * | 1/1999 | Yamaya | ............. | A61B 1/00091 600/121 |
| 5,865,726 A * | 2/1999 | Katsurada | ............ | A61B 1/0008 600/121 |
| 6,605,035 B2 * | 8/2003 | Ando | .................... | A61B 1/0008 600/127 |
| 6,878,107 B2 * | 4/2005 | Hino | .................... | A61B 1/0008 600/121 |
| 6,916,284 B2 * | 7/2005 | Moriyama | ......... | A61B 1/00089 600/127 |
| 8,038,604 B2 * | 10/2011 | Hamazaki | ............ | A61B 1/0008 600/107 |
| 8,747,304 B2 * | 6/2014 | Zeiner | ................ | A61B 1/00087 600/104 |
| 8,870,754 B2 * | 10/2014 | Wood | ..................... | A61B 1/018 600/107 |
| 2010/0240954 A1 * | 9/2010 | Wood | ..................... | A61B 1/018 600/114 |
| 2016/0374537 A1 * | 12/2016 | Chae | .................. | A61B 1/00089 600/127 |
| 2017/0000317 A1 * | 1/2017 | Iizuka | ...................... | A61B 1/00 |

FOREIGN PATENT DOCUMENTS

| | | |
|---|---|---|
| JP | 2001-333879 A | 12/2001 |
| JP | 2010-253061 A | 11/2010 |

OTHER PUBLICATIONS

Japanese Office Action dated Mar. 1, 2016 issued in JP 2015-556888.

* cited by examiner

ENDOSCOPE

CROSS REFERENCE TO RELATED APPLICATION

This application is a continuation application of PCT/JP2015/060465 filed on Apr. 2, 2015 and claims benefit of Japanese Application No. 2014-160714 filed in Japan on Aug. 6, 2014, the entire contents of which are incorporated herein by this reference.

BACKGROUND OF THE INVENTION

1. Field of the Invention

The present invention relates to an endoscope in which a cover is attached to a distal end member configuring a distal end portion of an endoscope main body.

2. Description of the Related Art

There has been known an endoscope in which a high-frequency treatment instrument is used. The endoscope of this type has structure in which, in order to safely use the high-frequency treatment instrument, a surface of an elongated insertion section is coated with an insulative resin material, an insulative rubber member is further disposed in an exterior portion of a bending section disposed on a distal end side of the insertion section, and a cover formed of an insulative material is attached to a distal end member configuring the distal end portion of the insertion section to insulate the entire insertion section of the endoscope. Since the distal end member is rigid, by attaching the cover, when an insertion section distal end is inserted into a bent body cavity of a human body or the like, even if the insertion section distal end touches a body cavity inner wall, it is possible to protect the body cavity inner wall from damage.

When safety is taken into account, the cover is desirably fixed to the distal end member by an adhesive. However, the endoscope needs to be sufficiently cleaned and disinfected after use. For example, when a mechanical component such as a raising base for raising a treatment instrument is housed in the distal end member, gaps among respective components are narrow and cleaning work takes time.

Therefore, for example, Japanese Patent Application Laid-Open Publication No. 2010-253061 discloses an endoscope in which a cover is enabled to be attached and detached, in cleaning and disinfection, the cover is detached from a distal end member to make it easy to clean both of the cover and the distal end member, and the cover can be attached to the distal end member after the cleaning.

In the endoscope disclosed in the literature, a guide groove extending from a distal end side in a proximal end direction and bending in a J-shape on a proximal end side is provided on a side surface of an end portion and, on the other hand, a convex section engaging with the guide groove is provided on an inner wall of the cover. That is, in a state in which the convex section of the cover engages with the guide groove, when the cover is attached to the distal end member, the convex section is guided by the guide groove to move. A projecting section protrudingly provided in the distal end member presses and elastically deforms an inner surface of the cover. At that point, the convex section has reached a J-shaped bending part of the guide groove. Therefore, by slightly returning the cover, the convex section hooks on a J-shaped bending end portion of the guide groove to be positioned and fixed.

SUMMARY OF THE INVENTION

An endoscope according to an aspect of the present invention includes: a distal end member configuring a distal end portion in an endoscope main body; a guide groove provided in the distal end member to extend from a proximal end side toward a distal end side; a first concave section provided on a proximal end side in the guide groove; a second concave section provided on a distal end side in the guide groove to be spaced a predetermined interval from the first concave section; a cover formed of an insulative material, the cover being attached to the distal end member; and a convex section provided in the cover, the convex section sliding in the guide groove to selectively engage with the first concave section and the second concave section.

An endoscope according to another aspect includes: a distal end member configuring a distal end portion in an endoscope main body; a convex section disposed on the distal end member; a cover formed of an insulative material, the cover being attached to the distal end member; a guide groove provided in the cover to extend from a proximal end side toward a distal end side; and a first concave section provided in a distal end direction and a second concave section provided in a proximal end direction, the first concave section and the second concave section being provided in the guide groove, the convex section sliding in the guide groove to selectively engage with the first concave section and the second concave section.

DETAILED DESCRIPTION OF THE PREFERRED EMBODIMENTS

Embodiments of the present invention are explained below with reference to the drawings. Note that the drawings are schematic and relations between thicknesses and widths of respective members, ratios of the thicknesses of the respective members, and the like are different from real ones. It goes without saying that portions, relations and ratios of dimensions of which are different from one another, are included among the drawings.

First Embodiment

Figure 1:
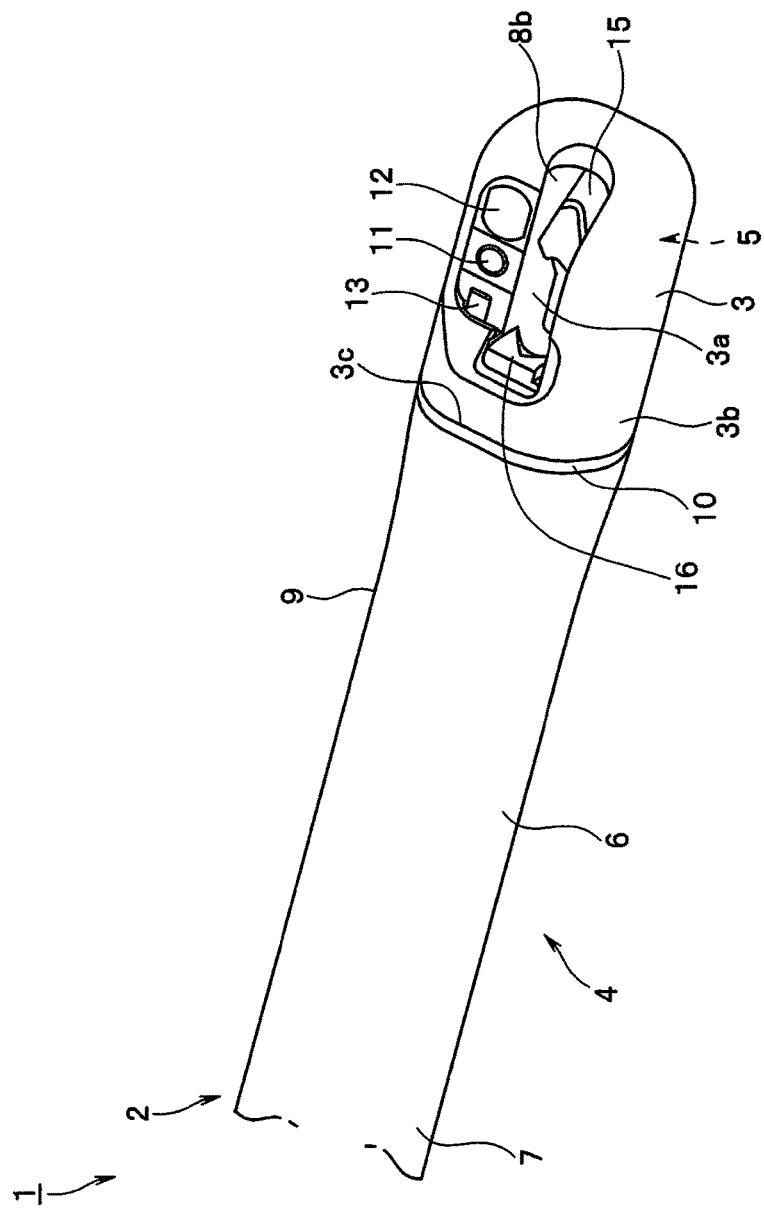
FIG. 1 is a perspective view on a distal end side of an endoscope according to a first embodiment.

A first embodiment of the present invention is shown in FIG. 1 to FIG. 8. In FIG. 1, a main part of an endoscope 1 is shown. The endoscope 1 includes an endoscope main body 2 and a cover 3. As the endoscope main body 2, in the present embodiment, a side-view type endoscope is shown. The endoscope main body 2 includes an elongated insertion section 4. An operation section (not shown in the figure), which a surgeon grasps to perform various kinds of operation, is provided on a hand side of the insertion section 4. The insertion section 4 is configured by continuously providing, from a distal end side, a distal end member 5 configuring a distal end portion, a bending section 6 bendable up and down and to left and right by concatenating a not-shown plurality of bending pieces, and a flexible tube section 7.

As shown in FIG. 1 and FIG. 3 to FIG. 5, the distal end member 5 includes a rigid distal-end-portion main body 8 made of a metal material. The flexible tube section 7 configuring the bending section 6 is concatenated at a proximal end of the distal-end-portion main body 8. Outer surfaces of the bending section 6 and the flexible tube section 7 are coated with a bending rubber 9 functioning as an insulating member. An end portion of the bending rubber 9 is connected to the proximal end of the distal-end-portion main body 8. A connecting section 8a, a cross section of which is formed in a substantially rounded-corner square shape, is formed in a base of the distal-end-portion main body 8. A ring-like elastic member 10, a cross section of which is formed in a rectangular shape, is attached to an end portion of the connecting section 8a. A rear surface of the elastic member 10 is closely attached to an opening end portion of the bending rubber 9. The elastic member 10 is formed of a material having elasticity and having electric insulation such as silicon rubber.

On an upper surface one side on the distal end side of the distal-end-portion main body 8, an observation window for side view (hereinafter simply referred to as "observation window") 11 and an illumination window 12, which radiates illumination light on an observation visual field, are disposed from the base side along an axial direction. Further, an air/water feeding nozzle 13 for cleaning the observation window 11 with air/water feeding or the like is disposed on the base side. Further, a housing chamber 8b is formed in a position adjacent to the observation window 11 and the illumination window 12 of the distal-end-portion main body 8. An end portion of a forceps channel (not shown in the figure) provided in the insertion section 4 is opened in the base of the housing chamber 8b.

Further, in the housing chamber 8b, a forceps raising base 15 that bends, in a desired direction, a treatment instrument 14 (see FIG. 6 and FIG. 7) such as forceps inserted through the forceps channel, a block member 16 that avoids contact with the distal-end-portion main body 8 when the treatment instrument 14 is bent, and the like are disposed as predetermined. Note that reference sign 8c in FIG. 6 and FIG. 7 denotes a passage through which a light guide fiber for transmitting illumination light to the illumination window 12 is inserted. Reference sign 8d in FIG. 6 denotes a housing section in which an image pickup section that picks up an object image made incident from the observation window 11 and formed as predetermined is housed.

The distal-end-portion main body 8 is electrically insulated by the cover 3 attached to an outer circumference of the distal-end-portion main body 8. The cover 3 has both of flexibility and electric insulation. The cover 3 is formed using, for example, synthetic resin represented by low-density polyethylene (LDPE) having flexibility, elastomer, or a rubber material.

Figure 6:
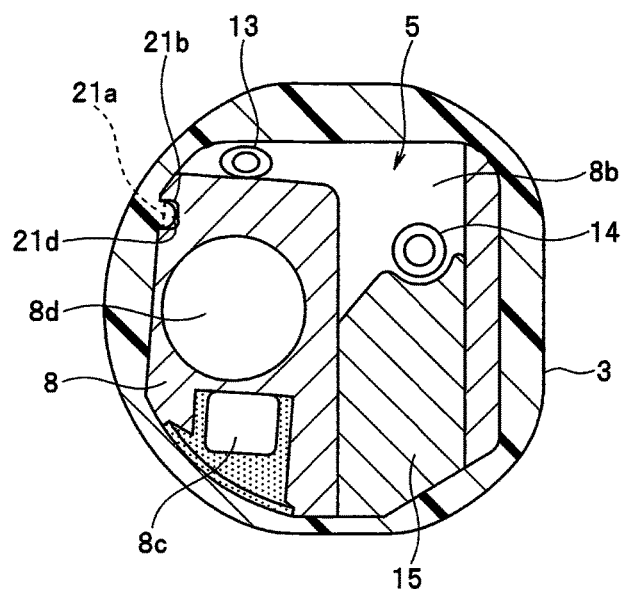
FIG. 6 is a VI-VI sectional view of FIG. 2 according to the first embodiment.
Figure 7:
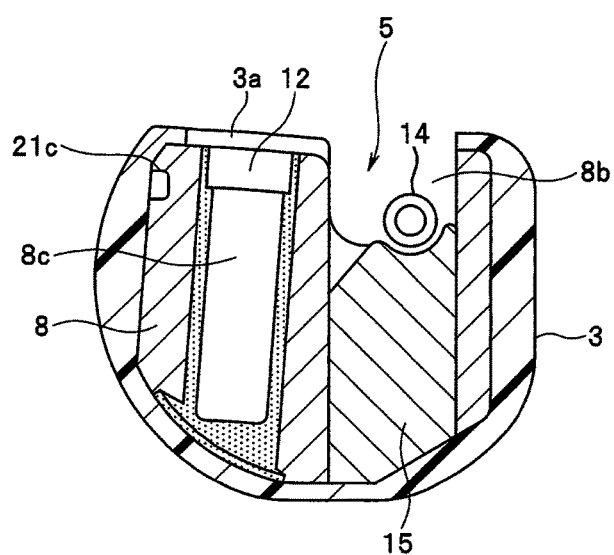
FIG. 7 is a VII-VII sectional view of FIG. 2 according to the first embodiment.

The cover 3 is formed in a cap shape including an opening window 3a that exposes the observation window 11, the illumination window 12, the forceps raising base 15, and the like as predetermined. Further, as shown in FIG. 6 and FIG. 7, an inner circumference of the cover 3 is formed in a shape substantially conforming to an external shape of the distal-end-portion main body 8. The cover 3 is enabled to slide along the outer circumference of the distal-end-portion main body 8.

The distal-end-portion main body 8 is formed by a substantial polygon (a non-rotary body) including plane sections and the like, longitudinal sectional outer circumferences of which cross one another. Therefore, when the cover 3 is attached to the distal-end-portion main body 8, rotation in an axial direction is restricted and only movement in a front-back direction is permitted. Further, in a state in which the cover 3 is attached to the distal-end-portion main body 8, a proximal end portion 3b of the cover 3 is set in surface contact with a connecting section 8a of the distal-end-portion main body 8 and is indirectly pressed against the bending rubber 9 in a state in which an opening end 3c of the cover 3 elastically deforms the elastic member 10.

A guide groove 21a is provided on one side of the distal-end-portion main body 8 to extend horizontally from a proximal end side toward a distal end side direction. Further, a first concave section 21b and a second concave section 21c are disposed at a predetermined interval apart from each other on the proximal end side and the distal end side in the guide groove 21a.

On the other hand, a convex section 21d is provided on an inner surface of the cover 3 opposed to the guide groove 21a provided on the one side of the distal-end-portion main body 8. The convex section 21d is enabled to slide in the guide groove 21a and enabled to selectively engage with the first and second concave sections 21b and 21c. The convex section 21d is a columnar body, a distal end of which is formed in a spherical shape. The first and second concave sections 21b and 21c are formed in a size capable of fixing the convex section 21d without causing a backlash when the convex section 21d engages with the first and second concave sections 21b and 21c.

Figure 4:
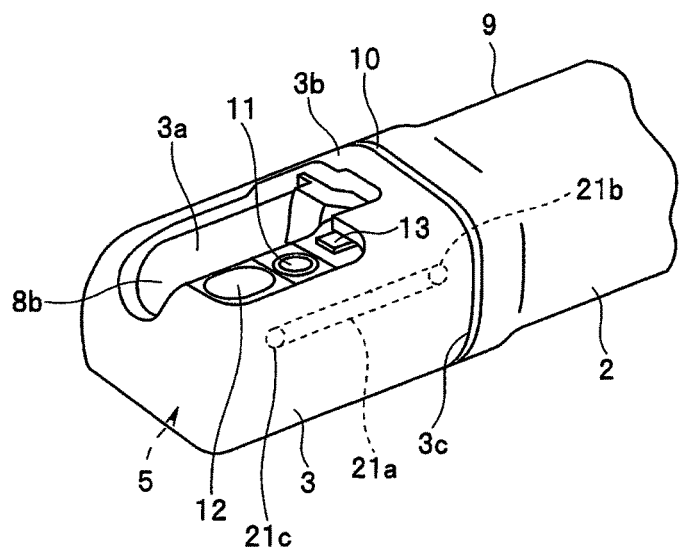
FIG. 4 is a main part perspective view of FIG. 1 according to the first embodiment.
Figure 5:
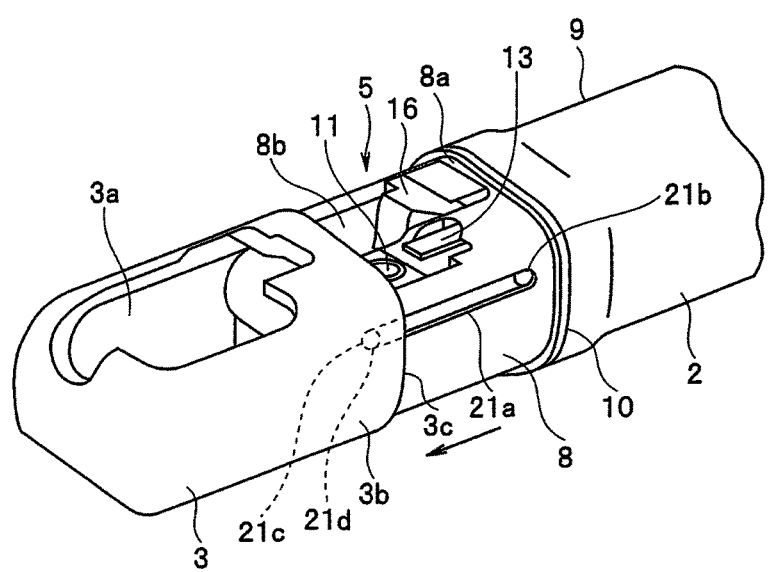
FIG. 5 is a main part perspective view of FIG. 3 according to the first embodiment.
Figure 8A:
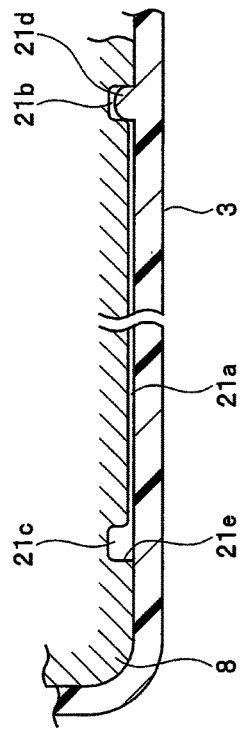
FIG. 8A is a VIII-VIII main part sectional view of FIG. 2 according to the first embodiment.
Figure 8B:
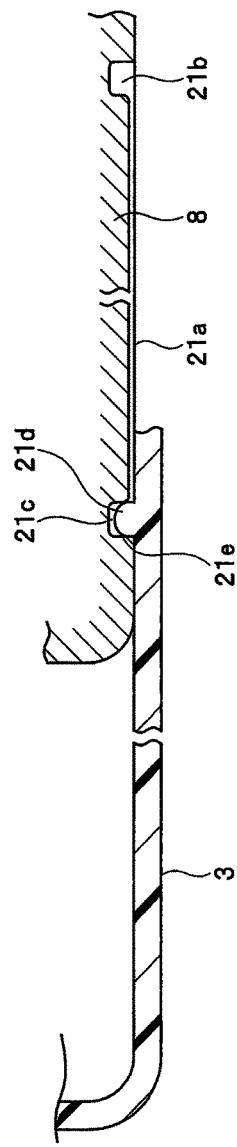
FIG. 8B is a main part sectional view of a state in which the cover shown in FIG. 8A is slid forward according to the first embodiment.

As shown in FIG. 4 and FIG. 8A, in a state in which the convex section 21d engages with the first concave section 21b, the opening end 3c of the cover 3 is pressed against the bending rubber 9 via the elastic member 10 and fixed. On the other hand, as shown in FIG. 5 and FIG. 8B, in a state in which the convex section 21d engages with the second concave section 21c, the cover 3 moves to the distal end side and is fixed in a position deviating from the distal-end-portion main body 8, that is, a position where the forceps raising base 15 in the housing chamber 8b is exposed from the proximal end side of the opening end 3c of the cover 3. A distal-end-side inner wall surface 21e of the second concave section 21c is formed more steeply than other wall surfaces of the same second concave section 21c, that is, an inner wall surface of the second concave section 21c is erected substantially perpendicularly to an outer surface and a ridge section of the second concave section 21c is formed at a right angle.

Consequently, in a state in which the second concave section 21c is provided in the distal-end-portion main body 8, a wall on the distal end side of the first concave section 21b is higher than a sidewall of the guide groove 21a. Therefore, it is difficult for the convex section 21d to climb over the second concave section 21c. As a result, the cover 3 less easily deviates further in a distal end direction than the distal-end-portion main body 8.

Action in the present embodiment by the configuration explained above is explained. In a state in which the cover 3 is attached to the distal end member 5, as shown in FIG. 6 and FIG. 8A, the convex section 21d formed in the cover 3 is engaged with the first concave section 21b formed on the base side of the distal-end-portion main body 8 and is fixed in a positioned state.

Figure 2:
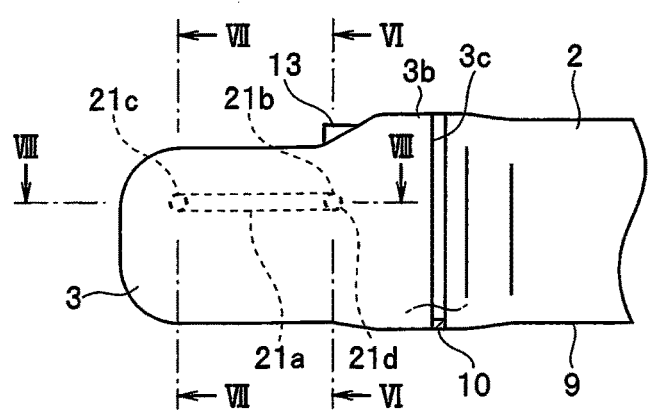
FIG. 2 is a side view on the distal end side of the endoscope according to the first embodiment.

In this state, as shown in FIG. 1, FIG. 2, and FIG. 4, the distal end member 5 is covered with the cover 3 and electrically insulated. An inner circumference of the proximal end portion 3b of the cover 3 is set in surface contact with a connecting section 8a formed in the base of the distal-end-portion main body 8. Further, the opening end 3c elastically deforms the elastic member 10 having electric insulation and is pressed against an opening end of the bending rubber 9. As a result, the cover 3 and the bending rubber 9 are closely attached. Therefore, when a high-frequency treatment instrument is used, a high-frequency current does not leak from between the cover 3 and the bending rubber 9.

On the other hand, in cleaning and disinfecting the distal end member 5 of the endoscope 1 after use, first, an operator pinches the cover 3 with fingers and pulls out the cover 3 in the distal end direction. Then, the convex section 21d formed on the inner surface of the cover 3 and the first concave section 21b are disengaged. The convex section 21d elastically deforms the cover 3 and runs on the guide groove 21a formed on the side surface of the distal-end-portion main body 8.

Figure 3:
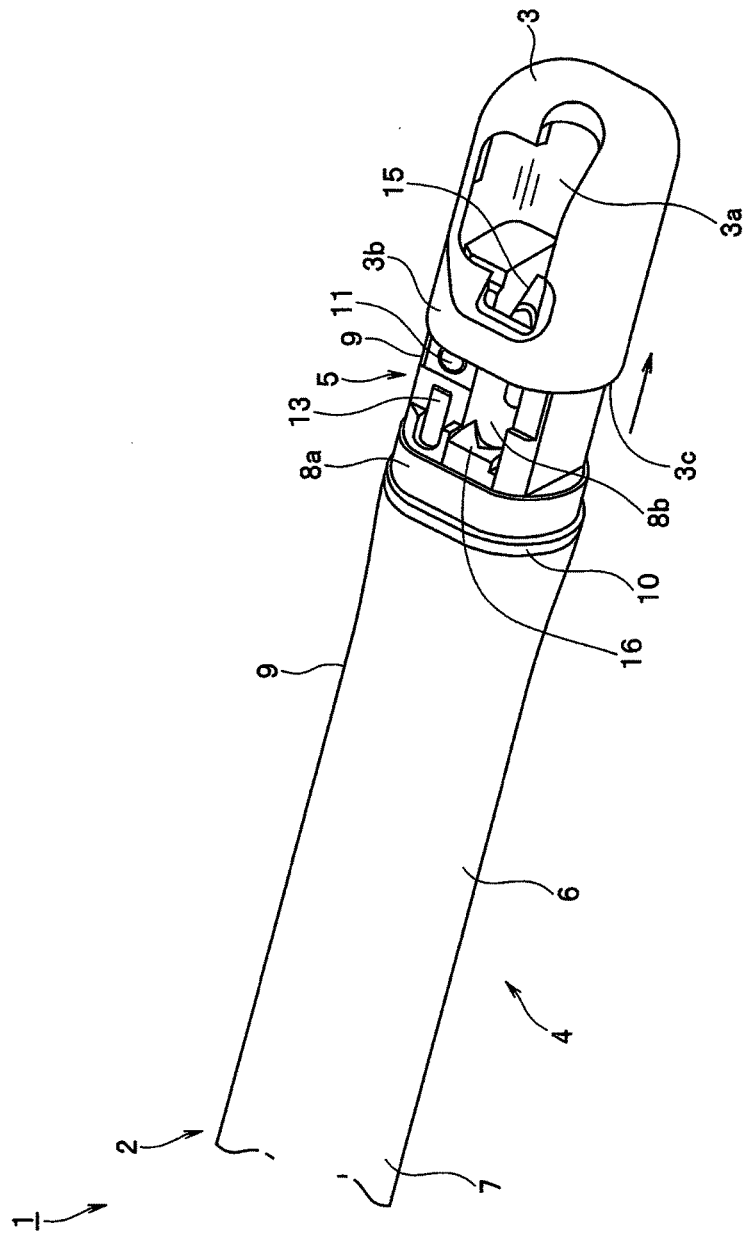
FIG. 3 is a perspective view of a state in which a cover is slid from the distal end side of the endoscope shown in FIG. 1 according to the first embodiment.

When the cover 3 is further pulled in the distal end direction in that state, the convex section 21d slides along the guide groove 21a. Therefore, the cover 3 is pulled out in the distal end direction. When the convex section 21d engages with the second concave section 21c, as shown in FIG. 3, FIG. 5, and FIG. 8B, the cover 3 is fixed to the distal end member 5 in a state in which the cover 3 deviates to the distal end side.

Then, the forceps raising base 15 and components around the forceps raising base 15 housed in the housing chamber 8b formed in the distal-end-portion main body 8 are exposed from a rear of the opening end 3c of the cover 3. The entire distal end member 5 including the forceps raising base 15 and the components around the forceps raising base 15 is cleaned and disinfected from this exposed part as predetermined. Further, the inner and outer surfaces of the cover 3 are cleaned and disinfected from the exposed part.

In a state in which the cover 3 is pulled out from the distal end member 5, the convex section 21d formed in the cover 3 engages with the second concave section 21c formed in the distal-end-portion main body 8. The second concave section 21c fixes the convex section 21d without causing a backlash. The distal-end-side inner wall surface 21e is formed steeply. Therefore, in the cleaning and the disinfection, the cover 3 does not come off the distal-end-portion main body 8.

The cover 3 is fixed in a state in which the cover 3 is pulled out from the distal-end-portion main body 8. Therefore, after the cleaning and the disinfection, it is possible to dry the cover 3 in the state in which the cover 3 is pulled out from the distal-end-portion main body 8. It is possible to easily remove water drops. Therefore, it is possible to achieve a reduction in a drying treatment time. Moreover, since the cover 3 is fixed to the distal-end-portion main body 8 and does not come off, it is easy to manage the cover 3.

After the cleaning and the disinfection of the distal end member 5 and the cover 3 are completed or drying treatment after the cleaning and the disinfection is completed, the operator pinches the cover 3 pulled out from the distal end member 5 and attaches the cover 3 to the distal end member 5. Then, the convex section 21d formed in the cover 3 elastically deforms the cover 3, runs on and engages with the guide groove 21a, and slides in a direction of the first concave section 21b along the guide groove 21a.

In the cleaning and the disinfection, the cover 3 does not come off the distal end member 5 and is fixed in the pulled out state. Therefore, the cover 3 is not mistaken and can be easily attached again. As a result, it is easy to manage the cover 3. It is possible to obtain satisfactory handlability.

The inner circumference of the cover 3 is formed in a shape substantially the same as a shape of the outer circumference of the distal-end-portion main body 8. Therefore, when the cover 3 is attached again, movement in a rotating direction is restricted. The inner circumference of the cover 3 slides using the outer circumference of the distal-end-portion main body 8 as a guide and moves in a direction of the connecting section 8a formed on the proximal end side. As a result, when the cover 3 slides on the distal-end-portion main body 8, the cover 3 does not move in the rotating direction. Therefore, unreasonable attachment in a positionally deviated state is not performed. It is possible to prevent damage or fixation of the cover 3. It is possible to obtain satisfactory workability.

When the opening end 3c of the cover 3 is pressed against the elastic member 10 and elastically deforms the elastic member 10 to press the opening end of the bending rubber 9, the convex section 21d formed on the inner surface of the cover 3 engages with the first concave section 21b formed in the base of the guide groove 21a (see FIG. 8A) and is fixed and set in an initial position as predetermined. The operator can grasp, with a sense of click at a time when the convex section 21d fits in the first concave section 21b, completion of the attachment of the cover 3. Therefore, the operator can surely attach the cover 3 to the distal end member 5.

In this way, according to the present embodiment, in the state in which the cover 3 is pulled out from the distal end member 5, the convex section 21d protrudingly provided on the inner surface of the cover 3 engages with the second concave section 21c formed in the distal-end-portion main body 8 and is fixed. Therefore, in the cleaning and the disinfection, the cover 3 does not come off. When the cover 3 is attached again, the convex section 21d can be returned to the initial position by being moved along the guide groove 21a formed in the distal-end-portion main body 8 and engaging with the first concave section 21b. Therefore, the cover 3 is not mistaken. As a result, it is easy to manage the cover 3. It is possible to obtain satisfactory handlability. Further, the cover 3 is attached to the distal-end-portion main body 8 in the state in which the movement in the rotating direction is restricted. Therefore, the cover 3 is not attached in a state in which the cover 3 positionally deviates in the rotating direction. When the cover 3 is attached again, the cover 3 is not damaged or fixed.

Second Embodiment

Figure 9:
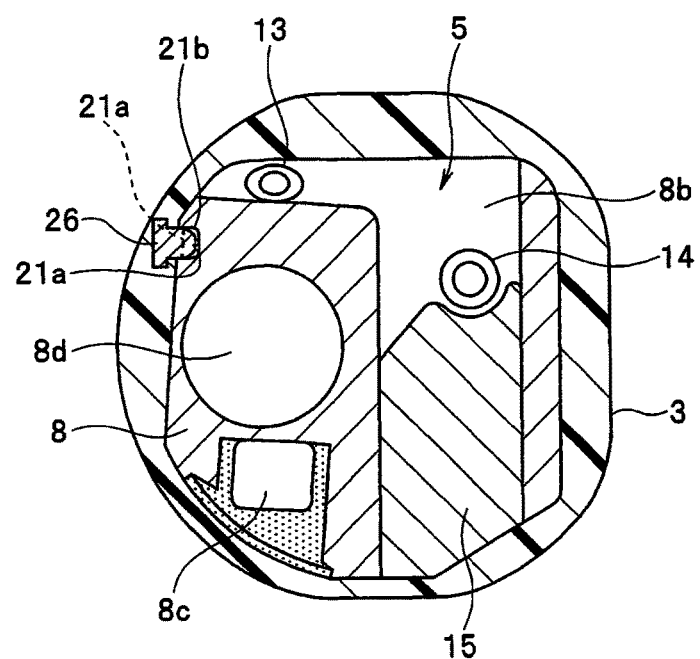
FIG. 9 is a sectional view equivalent to FIG. 6 according to a second embodiment.
Figure 10:
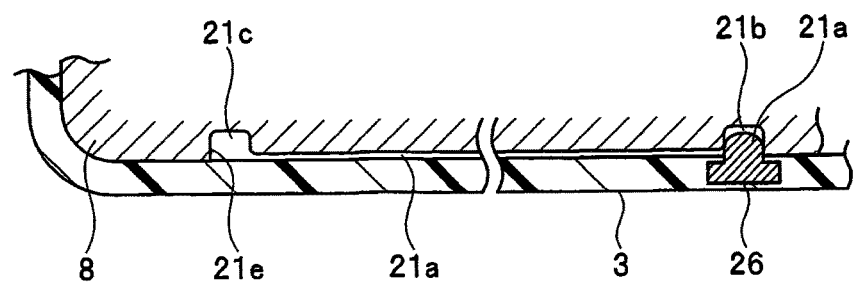
FIG. 10 is a sectional view equivalent to FIG. 8A according to the second embodiment.

A second embodiment of the present invention is shown in FIG. 9 and FIG. 10. Note that components same as the components in the first embodiment are denoted by the same reference numerals and signs and explanation of the components is omitted.

If the cover 3 is formed of a material that is easily elastically deformed such as soft rubber material, when the convex section 21d moves in the guide groove 21a and in a state in which the convex section 21d engages with the first and second concave sections 21b and 21c, it is likely that the convex section 21d itself is elastically deformed and easily comes off.

Therefore, in the present embodiment, the convex section 21d is formed of a rigid member 26 made of a metal member or the like. The rigid member 26 is insert-molded into the cover 3. Consequently, even if the cover 3 is formed of soft rubber or the like, the convex section 21d itself is not elastically deformed. It is possible to smoothly move the guide groove 21a. It is possible to maintain a state in which the convex section 21d engages with the first and second concave sections 21b and 21c. Note that action and effects in pulling out the cover 3 and attaching the cover 3 again are the same as the action and effects in the first embodiment explained above. Therefore, explanation of the action and effects is omitted.

Third Embodiment

A third embodiment of the present invention is shown in FIG. 11. Note that components same as the components in the first embodiment are denoted by the same reference numerals and signs and explanation of the components is omitted.

In the first embodiment explained above, the guide groove 21a and the first and second concave sections 21b and 21c are formed in the distal-end-portion main body 8 and the convex section 21d is formed in the cover 3. However, in the present embodiment, the guide groove 21a and the first and second concave sections 21b and 21c are formed on the inner surface of the cover 3 and the convex section 21d is formed in a position opposed to the guide groove 21a in the distal-end-portion main body 8.

Figure 11A:
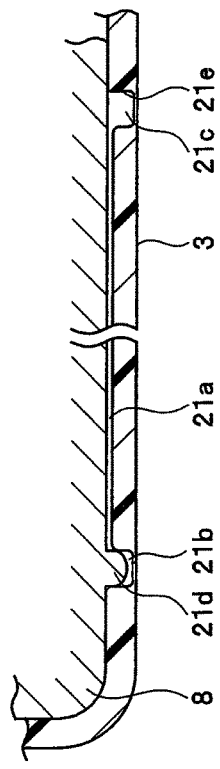
FIG. 11A is a sectional view equivalent to VIII-VIII in FIG. 2 according to a third embodiment.

Therefore, the cover 3 slides to advance and retract in a state in which the guide groove 21a formed on the inner surface of the cover 3 and the first and second concave sections 21b and 21c formed at both ends of the cover 3 are supported by the convex section 21d formed on the distal-end-portion main body 8. As shown in FIG. 11A, in a state in which the cover 3 is attached to the distal end member 5, the first concave section 21b formed at a distal end in the guide groove 21a provided on the inner surface of the cover 3 to extend from a proximal end side to a distal end side engages with the convex section 21d and fixed.

Figure 11B:
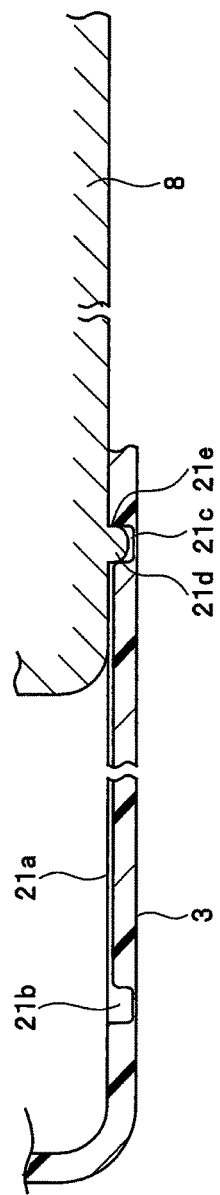
FIG. 11B is a sectional view of a state in which a cover shown in FIG. 11A is slid forward according to the third embodiment.

On the other hand, when the cover 3 is pulled out from the distal end member 5, as shown in FIG. 11B, the first concave section 21b is elastically deformed, comes off the convex section 21d, and slides in a state in which the guide groove 21a is supported by the convex section 21d. When the second concave section 21c formed at a proximal end in the guide groove 21a engages with the convex section 21d, the cover 3 is fixed to the distal end member 5 in a state in which the cover 3 deviates to the distal end side. Consequently, the forceps raising base 15 and components around the forceps raising base 15 housed in the housing chamber 8b formed in the distal-end-portion main body 8 are exposed from a rear of the opening end 3c of the cover 3 (for all of the components, see FIG. 3 and FIG. 5).

In a state in which the second concave section 21c is provided in the cover 3, a wall on the proximal end side of the second concave section 21c is higher than a sidewall of the guide groove 21a. Therefore, it is difficult for the convex section 21d to climb over the second concave section 21c. The cover 3 less easily deviates further in a distal end direction than the distal-end-portion main body 8.

In this case, the first and second concave sections 21b and 21c may be formed of a rigid member and insert-molded into the cover 3. Alternatively, a rigid member obtained by integrally forming the guide groove 21a and both the concave sections 21b and 21c may be insert-molded into the cover 3. Note that action and effects other than the action and effects explained above are the same as the action and effects in the first embodiment. Therefore, explanation of the action and effects is omitted.

The present invention is not limited to the respective embodiments explained above. For example, the elastic member 10 closely attached to the opening end of the bending rubber 9 may be removed. The opening end 3c of the cover 3 may be directly set in contact with and pressed against the opening end of the bending rubber 9. An endoscope regarded as the subject matter of the present invention is not limited to the side-view type endoscope. The invention of the present application can be applied to any endoscope as long as a distal-end-portion main body is covered with a cover. For example, an endoscope may be configured such that, when an insulated ring-like non-elastic member is used instead of the elastic member 10, the bending rubber 9 is closely attached to the non-elastic member and fixed during assembly, and, at the same time, the cover 3, which is an elastic body, is fixed to the distal end portion, the proximal end portion 3b closely attaches to the non-elastic member while being deformed.

What is claimed is:

1. An endoscope comprising:
a distal end member configuring a distal end portion in an endoscope main body;
a guide groove provided in the distal end member, the guide groove extending from a proximal end side toward a distal end side;
a first concave section provided on the proximal end side of the guide groove, the first concave section being formed deeper than the guide groove;
a second concave section provided on the distal end side of the guide groove to be spaced a predetermined interval from the first concave section, the second concave section being formed deeper than the guide groove;
a cover formed of an insulative material, the cover being attached to the distal end member such that a rotating movement of the cover is restricted; and
a convex section provided in the cover, the convex section sliding in the guide groove between the proximal end side and the distal end side to selectively engage with, and to be positioned at, the first concave section and the second concave section.

2. The endoscope according to claim 1, wherein the convex section engages with the first concave section to fix the cover in a state in which an outer surface of the distal end member is covered with the cover, and the convex section engages with the second concave section to fix the cover in a state in which a part of the outer surface of the distal end member is exposed to an outside.

3. The endoscope according to claim 1, wherein the distal end member is connected to a bending section covered with an insulating member, and, when the convex section engages with the first concave section and the cover is fixed to the distal end member, the cover and the insulating member are in contact directly or in contact indirectly while deforming an insulated elastic member.

4. The endoscope according to claim 1, wherein the cover is configured by an elastic member, and the convex section provided in the cover is configured by a rigid member.

5. The endoscope according to claim 1, wherein the first and second concave sections are disposed at both ends of the guide groove.

6. The endoscope according to claim 1, wherein a distal-end-side inner wall surface of the second concave section is formed more steeply than other wall surfaces.

7. The endoscope according to claim 1, wherein a distal-end-side inner wall surface of the second concave section is formed to be substantially perpendicular to the guide groove.

\* \* \* \* \*